US009801905B2

United States Patent
Mohamed et al.

(10) Patent No.: US 9,801,905 B2
(45) Date of Patent: Oct. 31, 2017

(54) USE OF ORGANIC SULPHUR, ANTIOXIDANTS, AND AMINO ACIDS IN CONJUNCTION WITH EXERCISE AND ELECTROMAGNETIC STIMULATION TO TREAT OSTEOPOROSIS

(71) Applicants: Hossam Abdel Salam El Sayed Mohamed, Ottawa (CA); Houda Abdul Rahman M. Al Mansour, Ottawa (CA)

(72) Inventors: Hossam Abdel Salam El Sayed Mohamed, Ottawa (CA); Houda Abdul Rahman M. Al Mansour, Ottawa (CA)

( * ) Notice: Subject to any disclaimer, the term of this patent is extended or adjusted under 35 U.S.C. 154(b) by 0 days.

(21) Appl. No.: 15/124,101

(22) PCT Filed: Mar. 13, 2014

(86) PCT No.: PCT/IB2014/000366
§ 371 (c)(1),
(2) Date: Sep. 7, 2016

(87) PCT Pub. No.: WO2015/136319
PCT Pub. Date: Sep. 17, 2015

(65) Prior Publication Data
US 2017/0071977 A1    Mar. 16, 2017

(51) Int. Cl.
| | | |
|---|---|---|
| *A61K 33/04* | (2006.01) | |
| *A61K 31/198* | (2006.01) | |
| *A61K 31/385* | (2006.01) | |
| *A61K 45/06* | (2006.01) | |
| *A61K 31/10* | (2006.01) | |
| *A61K 41/00* | (2006.01) | |
| *A61K 9/00* | (2006.01) | |
| *A61N 2/00* | (2006.01) | |

(52) U.S. Cl.
CPC ............ *A61K 33/04* (2013.01); *A61K 9/0053* (2013.01); *A61K 31/10* (2013.01); *A61K 31/198* (2013.01); *A61K 31/385* (2013.01); *A61K 41/00* (2013.01); *A61K 45/06* (2013.01); *A61N 2/002* (2013.01)

(58) Field of Classification Search
CPC ..................................................... A61K 33/04
USPC ........................................................ 514/436
See application file for complete search history.

(56) References Cited

U.S. PATENT DOCUMENTS

| | | |
|---|---|---|
| 5,478,303 A | 12/1995 | Foley-Nolan et al. |
| 5,518,496 A | 5/1996 | McLeod et al. |
| 6,132,362 A | 10/2000 | Tepper et al. |
| 6,179,772 B1 | 1/2001 | Blackwell |
| 6,261,221 B1 | 7/2001 | Tepper et al. |
| 6,418,345 B1 | 7/2002 | Tepper et al. |
| 6,524,233 B2 | 2/2003 | Markoll |
| 6,547,713 B1 | 4/2003 | Talpo |
| 6,839,595 B2 | 1/2005 | Tepper et al. |
| 7,175,587 B2 | 2/2007 | Gordon et al. |
| 8,376,925 B1 | 2/2013 | Dennis et al. |
| 8,496,971 B2 | 7/2013 | Gradl et al. |

FOREIGN PATENT DOCUMENTS

| | | |
|---|---|---|
| EP | 0048451 A1 | 3/1982 |
| EP | 1442766 B1 | 8/2009 |
| WO | 2005123059 A1 | 12/2005 |

OTHER PUBLICATIONS

McGean, The Sulfur Study (1999-2012), pp. 1-5.*
Cleveland Clinic: The Best Workout for Osteoporosis. (2012) pp. 1-9.*
International Search Report re PCT/IB2014/000366, dated Dec. 8, 2014.
The effect of alpha-lipoic acid in ovariectomy and inflammation-mediated osteoporosis on the skeletal status of rat bone, B Polat, Z Halici, E Cadirci, A Albayrak . . . —European journal of . . . , 2013—Elsevier.
Pulsed electromagnetic fields on postmenopausal osteoporosis in southwest China: A randomized, active-controlled clinical trial, HF Liu, L Yang, HC He, J Zhou, Y Liu . . . —. . . , 2013—Wiley Online Library.
Antioxidant α-lipoic acid inhibits osteoclast differentiation by reducing nuclear factor-κB DNA binding and prevents in vivo bone resorption induced by receptor . . . HJ Kim, EJ Chang, HM Kim, SB Lee, HD Kim . . . —Free Radical Biology . . . , 2006—Elsevier.
Pulsed electromagnetic fields prevent osteoporosis in an ovariectomized female rat model: A prostaglandin E2-associated process, K Chang, WHS Chang—Bioelectromagnetics, 2003—Wiley Online Library.
Human Osteopenic Bone-Derived Osteoblasts: Essential Amino Acids Treatment Effects P Torricelli, M Fini, G Giavaresi . . . — Artificial cells, blood . . . , 2003—Taylor & Francis.
Essential amino acids increase the growth and alkaline phosphatase activity in osteoblasts cultured in vitro MT Conconi, M Tommasini, E Muratori, PP Parnigotto—II Farmaco, 2001—Elsevier.
Wolff's Law, Bone Formation, Modeling and Remodeling http://teambone.com/education-basic/modelingremodeling/. Downloaded Sep. 7, 2016.
The Biomechanics of Wolff's Law: Recent Advances, P.J. Prendergast http://alexandria.tue.nl/repository/freearticles/585490.pdf. Downloaded Sep. 7, 2016.
Collagen: The Fibrous Proteins of the Matrix http://www.ncbi.nlm.nih.gov/books/NBK21582/. Downloaded Sep. 7, 2016.

(Continued)

*Primary Examiner* — Taofiq A Solola
(74) *Attorney, Agent, or Firm* — Caesar Rivise, PC (57) ABSTRACT

Through the use of a combination of naturally occurring substances, application of mechanical energy by way of exercise, and application of a pulsed electromagnetic field (PEMF), new bone formation at lines of stress can be promoted. This bone forming activity is useful in the treatment and prevention of osteoporosis. The naturally occurring substances consist of organic sulphur, antioxidants, and amino acids. These substances are preferably administered orally. In preferred embodiments, the antioxidant is alpha-lipoic acid, and the amino acid is selected from the group consisting of lysine, glutamine, and mixtures thereof.

18 Claims, 2 Drawing Sheets

(56) References Cited

OTHER PUBLICATIONS

Sulphur Deficiency http://www.westonaprice.org/health-topics/abcs-of-nutrition/sulfur-deficiency/. Downloaded Sep. 7, 2016.
Newly Discovered Alpha Lipoic Benefits, Downloaded Sep. 8, 2016.
Molecular biomechanics of collagen, shu-Wei Chang, et al. Downloaded Sep. 8, 2016.
The Dowsing Reaction Originates From Piezoelectric Effect in Bone, Downloaded Sep. 7, 2016.
Deformation micromechanisms of collagen fibrils under uniaxial tension, Downloaded Sep. 7, 2016.
Bone Remodeling, Derek Moore, Downloaded Sep. 7, 2016.
Morphological analysis of the proximal femur using quantitative, Downloaded Sep. 7, 2016.
Bisphosphonates are a class of drugs that prevent the Isos of bone mass, https://en.wikipedia.org/wiki/Bisphosphonate. Downloaded Sep. 7, 2016.
Mayo Clinic Proceedings, Adverse Effects of Bisphosphonates http://www.ncbi.nlm.nih.gov/pmc/articles/PMC2704135/. Downloaded Sep. 7, 2016.
Department of Physics and Measurement Technology, Piezoelectric Coatings on Implants, www.diva-portal.org/smash/get/diva2:20640/FULLTEXT01.pdf. Downloaded Sep. 7, 2016.
Origin of the Piezoelectric Effect in Bone, http://andrewamarino.com/PDFs/011-CalcTissRes1971.pdf. Downloaded Sep. 7, 2016.
Anti-Glycation Activity of Alpha-Lipoic, Anti-Aging Medicine, Downloaded Sep. 7, 2016.
Electrical Properties of Bone, Downloaded Sep. 7, 2016.
Dietary L-Lysine and calcium metabolism in humans, Downloaded Sep. 7, 2016.
L-Lysine, Alternative Medicine Review, vol. 12, No. 2 2007.
Relevance of Collagen Piezoelectricity to "Wolff's Law": A Critical Review, Downloaded Sep. 7, 2016.
Finite element 3D Modelling of Mechanical Behaviour of Mineralized Collagen Microfibrils, downloaded Sep. 6, 2016.
Jeremiah, et al., "Diagnosis and Management of Osteoporosis". Am Fam Physician. Aug. 15, 2015; 92(4)261-268.

* cited by examiner

USE OF ORGANIC SULPHUR, ANTIOXIDANTS, AND AMINO ACIDS IN CONJUNCTION WITH EXERCISE AND ELECTROMAGNETIC STIMULATION TO TREAT OSTEOPOROSIS

FIELD OF INVENTION

The present invention relates to the medical fields of bone growth and degeneration and more particularly the treatment of osteoporosis (OP).

BACKGROUND OF INVENTION

Osteoporosis is a disease of bone weakness in the elderly and also part of the general aging process. It is symptomless in most cases. When symptoms present, they usually present as either deep bone pain due to micro-fracture or even gross fracture of the bone due to mild trauma. Orthopedically, OP is defined as a reduction of bone mass per unit volume. This means that the bone loses substance leading the bone to become weak and easily fractured by milder traumas.

The bone is a biphasic material composed of two main components: Calcium hydroxyapatite (ceramic) and collagen protein. Ceramic comprises about 50% of the bone structure and gives the bone its glass-like rigidity. Collagen protein (bundle) comprises about 28% of the bone structure and gives the bone some degree of resilience, absorbing shock from trauma and protecting the bone from fracture by lessening its intensity. The remaining 22% of bone is comprised of water.

Present medications for the treatment of OP include bisphosphonates, in combination with Vitamin D, calcitonin and/or calcium supplementation. These medications have many side effects including: gastro-intestinal upset, headaches, drowsiness, atrial fibrillation, osteonecrosis of the jaw, oesophageal cancer, and subtrochanteric fracture of the femur (11, 12). Furthermore, treatments are expensive and can require long term dosing from 6 months up to 2 years or more for effect. Moreover, these medications are not 100% effective in correcting OP and normalizing bone density. Furthermore, these medications show marked patient variability in response regardless of the degree of bone loss.

The most important drawback of current medications and treatment regimens is that medications use in current treatment regimens correct bone loss only by affecting bone eating cells (osteoclasts) resulting in a new bone which is evenly distributed or a uni-phasic bone regardless of the lines of the stress. However, recent research (1, 2) shows that the starting point of new bone synthesis is by deformation of collagen bundles inside the bone matrix and not in bone cells. The collagen bundles deform in response to mechanical stress and produce an electrical gradient difference which is capable of stimulating bone forming cells to synthesize new bone at the sites of stress. The formation of new bone by mechanical stress was discovered in 1892 and was defined as Wolff's law, (1) & (19) (20). However, the electrical gradient difference (16), discovered later in 1963, was still not clear. With the aid of electron microscopic studies in 2007, the piezo-electric theory became clear: the compression side of collagen bundles show negative charges and are capable of stimulating bone forming cells (8). On the other hand, positive charges, arising on the tension side, are capable of stimulation bone eating cells (8). Hence, there is a need for treatments targeting this mechanism and other phases of OP pathology.

There is a continuous need for new medications for treatment of osteoporosis which are more effective, cheaper and with fewer side effects. The object of this invention is a treatment of osteoporosis with all of the above advantages by targeting the underlying pathology of OP and stimulating bone formation where it is most needed, at the lines of stress.

BRIEF SUMMARY OF THE INVENTION

The present invention treats OP at various stages of OP pathology to reverse OP in a manner with fewer side effects and yet advantageously promoting new bone formation at lines of stress for stronger and healthier bones (e.g., biphasic bone which is formed of denser bone at the lines of stress and less dense away from these lines).

The present invention provides for a treatment regimen for OP comprising: (a) organic sulphur, (b) antioxidants, (c) amino acids, (d) mechanical energy and (e) pulsed electromagnetic field (PEMF), wherein the regimen stimulates bone formation.

In certain embodiments, the organic sulphur, antioxidants and amino acids are orally administered. In certain embodiments, the organic sulphur comprises about 1.5 grams of organic sulphur administered twice a day. In certain embodiments, the antioxidants comprise about 500-750 mg of alpha lipoic acid administered twice a day.

In certain embodiments, the amino acids comprise at least one of lysine or glutamine. In certain embodiments, the amino acids comprise about 500-1000 mg of lysine administered twice a day. In certain embodiments, the amino acids comprise about 500-1000 mg of glutamine administered twice a day.

In certain embodiments, the mechanical energy comprises exercise. In certain embodiments the exercise is regular exercise. In certain embodiments, the exercise is non-vigorous with the use of PEMF. In certain embodiments, the PEMF is from a PEMF device. In certain embodiments, the PEMF comprises application of PEMF for about ½ hour, three times a week at an intensity of about 0.6 Tesla and 30 Hz.

In certain embodiments, the regimen is administered for a period of up to about 6 months. In certain embodiments, the regimen is administered for a period of up to about 2 years.

The present invention also provides a method of treating OP comprising therapeutically effective amounts of: (a) organic sulphur, (b) antioxidants, (c) amino acids, (d) mechanical energy and (e) pulsed electromagnetic field (PEMF).

In certain method embodiments, the organic sulphur, antioxidants and amino acids are orally administered. In certain method embodiments, the organic sulphur comprises about 1.5 grams of organic sulphur administered twice a day. In certain method embodiments, the antioxidants comprise about 500-750 mg of alpha lipoic acid administered twice a day.

In certain method embodiments, the amino acids comprise at least one of lysine or glutamine. In certain method embodiments, the amino acids comprise about 500-1000 mg of lysine administered twice a day. In certain method embodiments, the amino acids comprise about 500-1000 mg of glutamine administered twice a day.

In certain method embodiments, the mechanical energy comprises exercise. In certain embodiments the exercise is regular exercise. In certain method embodiments, the exercise is non-vigorous with the use of PEMF. In certain method embodiments, the PEMF is from a PEMF device. In certain method embodiments, the PEMF comprises application of PEMF for about ½ hour, three times a week at an intensity of about 0.6 Tesla and 30 Hz.

In certain method embodiments, the components are used in a regimen. In certain method embodiments, the regimen is administered for a period of up to about 6 months. In certain method embodiments, the regimen is administered for a period of up to about 2 years.

The present invention also provides for a kit comprising: (a) organic sulphur, (b) antioxidants, (c) amino acids and optionally a (d) pulsed electromagnetic field (PEMF) device wherein the components are designed for use in combination with mechanical energy in a regimen for treatment of osteoporosis by stimulating new bone formation with instructions therefor.

In certain embodiments, the kit comprises an oral dosage form of organic sulphur comprising about 1.5 grams of organic sulphur. In certain embodiments, the kit comprises an oral dosage form of the antioxidants comprising about 500-750 mg of alpha lipoic acid.

In certain embodiments, the kit comprises an oral dosage form of the amino acids comprising at least one of lysine or glutamine. In certain embodiments, the kit comprises an oral dosage form of the amino acids comprising about 500-1000 mg of lysine. In certain embodiments, the kit comprises an oral dosage form of the amino acids comprising about 500-1000 mg of glutamine.

In certain embodiments, the kit comprises each oral dosage form component in quantities sufficient for a regimen lasting about 6 months. In certain embodiments, the kit comprises single dose packs comprising the oral dosage forms of: (a) organic sulphur, (b) antioxidants, (c) amino acids and directions for use.

DETAILED DESCRIPTION OF THE INVENTION

There is a continuous need for new medications for treatment of OP which are more effective, cheaper and with fewer side effects. The object of this invention is a treatment of OP with all the above advantages by targeting the underlying pathology of OP and simulating bone formation where it is most needed, at the lines of stress.

Bone turnover is formed by two processes that happen simultaneously in opposing directions. One is construction and the other is resorption. Construction involves new bone formation by bone forming cells (Osteocytes and Osteoblasts), while resorption involves bone destruction by bone eating cells (Osteoclasts). In elderly patients over age 50, there is a reduction in the rate of new bone formation, while resorption stays the same. This change results in gradual bone loss.

Bisphosphonates, the main drugs for treatment of OP, only target Osteoclasts by inhibiting them from resorbing bone. Therefore, in patients treated with bisphosphonates, bone formation takes place without complimentary bone resorption/degradation (11). Recent studies show that although resorption causes bone weakness, it is also vital for renewal of the bone. Therefore, prolonged use of bisphosphonates causes the bone to be unhealthy, clinically presented as either subtrochanteric fracture of the femur, osteonecrosis of the jaw, and/or heavier bone, presenting as musculo skeletal pain, and others (12). The cause of the reduction of new bone formation in old age is due to two main factors. One such factor is the reduction of mechanical stress (e.g., exercise, running . . . etc.) as a result of a number of factors including: muscle weakness, painful joint due to arthritis and/or the more sedentary life style of the elderly. The other factor is the reduction of the amount of protein substances, collagen bundles, in the bone; either a quantitative reduction to be less than 28% or a qualitative reduction where there is decreased functional collagen bundles because of the glycation process (non-enzymatic attachment to glucose) or an organic sulphur deficiency. Recent research show that functional collagen bundles are connected to each other by sulphur bridges and an organic sulphur deficiency leads to the reduced sulphur bridges and dysfunctional collagen bundles (3).

Without being bound by theory, the subject invention treats OP by addressing these two factors of OP pathology.

Figure 3:
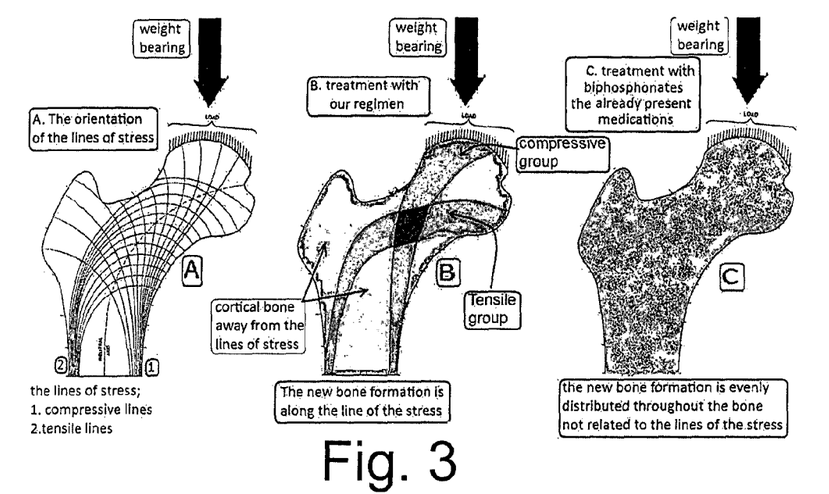
FIGS. 3a, 3b, and 3c are diagrams showing the concentration of bone formation in relation to lines of stress for the regimen of the present invention compared to conventional OP therapies.

Moreover, one of the most important biomechanical aspects of bone formation, protecting it from fracture, is uneven bone density (referred earlier as biphasic bone). Where bone is subjected to a higher stress, there is a denser concentration of bone material and the collagen bundles are linearly arranged along the lines of the stress. Away from these lines, the concentration of bone material is less dense because of a decreased need and the collagen bundles are haphazardly arranged. The area of denser bone is called bone trabeculae. These bone trabeculae are both denser and more resilient in the same time while surrounding areas of bone are less dense, but more rigid. The areas of trabecular and surrounding bone structure are depicted in FIG. 3b.

Bone trabeculae are arranged in accordance with the mechanical axis of the bone, which means the axial line of stress. The arrangement is complicated, but simply put: the trabeculae nearer the axis are called compressive trabeculae while those away from axis are called tensile trabeculae. The trabeculae are denser areas of concentrated bone substance and function to support body weight. These trabeculae are also more resilient and able to withstand a greater load without fracture because the collagen bundles are linearly arranged along the lines of the stress.

On the other hand, less dense bone is usually in the periphery of the bone nearer to the cortex. This bone is less dense but more rigid (e.g., glass-like) to accommodate muscle attachment. Moreover, these areas are also more vascular. The decreased density of this type of bone also contributes to making bones lighter thereby decreasing the load on muscles and joints. The collagen bundles in this type of bone are haphazardly arranged.

However, current medications, inhibiting bone resorption by bone eating cells (Osteoclasts) results in even distribution of new bone formation. As bone forming cells are not affected by current medications, the process of bone formation is unopposed. The resulting new bone would be of the same density at all different locations (i.e., uniphasic bone). This problem is recognized, for example, in U.S. Pat. No. 8,496,971 whose disclosure is incorporated by reference herein.

The present invention addresses all of the above drawbacks of the prior art and involves use of components in a treatment regimen for OP comprising: (a) organic sulphur, (b) antioxidants, (c) amino acids, (d) mechanical energy, and (e) pulsed electromagnetic field (PEMF). Each of these components of the subject regimen will now be addressed.

Sulphur deficiency causes bone collagen bundles to be easily glycated (non-enzymatic attachment of glucose). The collagen thus becomes dysfunctional. In the presence of dysfunctional collagen bundles, the conversion of mechanical energy to electrical energy is less than optimal compared to normal collagen, leading to a decrease in bone formation.

Recent research (3) shows that sulphur acts as bridges between collagen bundles and these bridges prevent or minimize the glycation effect of glucose on collagen bundles. Therefore, sulphur maintains the vitality of the collagen bundles i.e., it prevents collagen bundles from being dysfunctional ones. In old age, sulphur easily becomes deficient because sulphur is either destroyed by the heat of cooked foods or foods containing sulphur are rarely eaten due to its unpleasant odor, e.g., garlic, onion, cabbage, eggs, etc. Once the process of sulphur deficiency starts, it leads to dysfunctional collagen bundles and results in the reduction of the piezoelectric property of the collagen bundles responsible for new bone formation. This leads to decrease new bone formation, which in turn, leads to further suboptimal energy conversion because the amount of energy converted is proportional to the newly reduced bone formation and so on, i.e., decrease energy>leads to decrease in new bone>further decrease energy>further decrease of new bone>much further decrease energy production and so on (i.e., a vicious cycle).

Sulphur supplementation promotes connection of collagen bundles by disulphide bonds and results in functional collagen bundles insides the bone. Recent studies (4) also show that excess sulphur prevents glycation of collagen bundles. Glucose is a highly reducing agent, attacking collagen bundles causing their damage. The presence of surplus sulphur causes the glucose to attack (reduce) sulphur instead of collagen. Sulphur will not be damaged by the reducing effect of glucose because it has a very wide range of oxidative state, ranging from +6 to −2. Therefore, maintaining surplus sulphur prevents glycation of collagen (4). Thus, sulphur indirectly enhances more new bone formation by converting more of the mechanical stress into electrical currents, resulting in new bone formation by the piezoelectric property of bone (13, 14).

A therapeutically effective amount of organic sulphur is for example an amount that promotes, maintains, or inhibits loss of, functional collagen bundles in a subject with OP.

In a preferred embodiment, about 1.5 grams of organic sulphur is administered twice a day for a period of about 6 months. Organic sulphur is a natural substance not a chemical compound. It is already present in the human body in small amounts. Thus, the dose of the preferred embodiment is safe with no expected side effects.

However, as described, osteoporosis is a vicious cycle. Once the disease starts, sulphur supplementation can stop further progression. However, sulphur alone cannot reverse OP progress. Further medication is necessary for reversal of OP.

Antioxidants are substances that can neutralize toxic free radicals formed inside cells, making them harmless to tissue proteins like bone collagen. Antioxidants can also help in deglycation of already glycated collagen bundles.

In treating OP, antioxidant supplementation can help in converting dysfunctional collagen bundles to functional collagen bundles and minimizing the loss of the transformation of mechanical to electrical energy in stimulation of bone formation. By this process, antioxidant supplementation addresses the qualitative reduction of collagen bundles in OP by increasing the amount of functional collagen bundles.

A therapeutically effective amount of antioxidants is, for example, an amount that promotes, maintains, or inhibits loss of, functional collagen bundles in a subject with OP. Antioxidants of the invention may be any combination of materials that quenches a free radical. For example, foods such as ginkgo biloba, citrus pulp, grape pomace, tomato pomace, carrot and spinach as well as various other materials such as beta-carotene, selenium, coenzyme Q10 (ubiquinone), lutein, tocotrienols, soy isoflavones, S-adenosylmethionine, gluthathione, taurine, N-acetylcysteine, vitamin E, vitamin C, alpha-lipoic acid, L-carnitine and the like are antioxidants suitable for use in this invention.

In a preferred embodiment, the antioxidant is alpha lipoic acid which is natural substance present in our food but in a trace amount. The preferred dose of alpha lipoic acid is about 500-750 mg twice a day for a period of about 6 months. Experimental (5) studies show that alpha lipoic acid is indirectly associated with new bone formation because it partly inhibits the Osteoclasts (which are the cells responsible for the bone resorption). Therefore, the bone forming cells would function without the complimentary bone resorption resulting in new bone formation without bone degradation. Moreover, alpha-lipoic acid is considered one of the strongest antioxidants, with both anti-glycation and anti-oxidant function. Therefore, it will protect the collagen bundles from glycation and cure the already glycated ones into normal healthy collagen allowing more subsequent piezoelectric property reaction and subsequent new bone formation (15).

Amino acids are the building blocks of protein synthesis, including collagen bundles. They are natural substances that are present in our food but in quantities less than the therapeutic dose. Collagen bundles are made up of only three amino acids: glycine, proline and lysine. Of the three, only lysine is essential, meaning it is not synthesized by the human body and is sourced from food. A deficiency of lysine, for example as in the case of the diet of many vegetarians, leads to less than normal amounts of collagen. Moreover, recent studies (17) & (18) show that lysine supplementation improves the bone of osteoporotic patient because it helps in calcium re-absorption by the kidney and prevents its loss in urine.

Although not found in collagen bundles, a deficiency of glutamine can also indirectly contribute to the reduction in the amount of collagen bundles. To compensate for the deficiency of glutamine, the body breaks down collagen bundles to its component amino acids. It then uses the glycine component for the synthesis of glucose as a source of energy instead of glutamine. Normal or even surplus levels of glutamine can protect bone collagen from breakdown.

Supplementation of certain amino acids promotes normal amounts of bone collagen bundles. By this process, amino acids supplementation address the quantitative reduction of collagen bundles in OP by maintaining normal amounts of the collagen bundles in bone.

A therapeutically effective amount of amino acids is, for example, an amount that promotes, maintains, and inhibits loss of, functional collagen bundles in a subject with OP. Amino acids of the invention may be essential, nonessential or any derivative thereof. For example, any combination of the following: Arginine, Agmatine, Alanine, Asparagine, Selenocysteine, Serine, Citrulline, Creatine, Glutamine, Histidine, Isoleucine, Leucine, Norvaline, Ornithine, Valine, Aspartic Acid, Cysteine, Glycine, Lysine, Methionine, Proline, Tyrosine, and Phenylalanine, Tryptophan and the like may be used.

In a preferred embodiment of this invention, about 500-1000 mg of lysine is administered twice a day for a period of about 6 months. In another preferred embodiment about 500-1000 mg of glutamine is administered twice a day for a period of about 6 months. In yet another preferred embodiment, both lysine and glutamine are supplemented at the preferred dose and regimen as described above.

Figure 1:
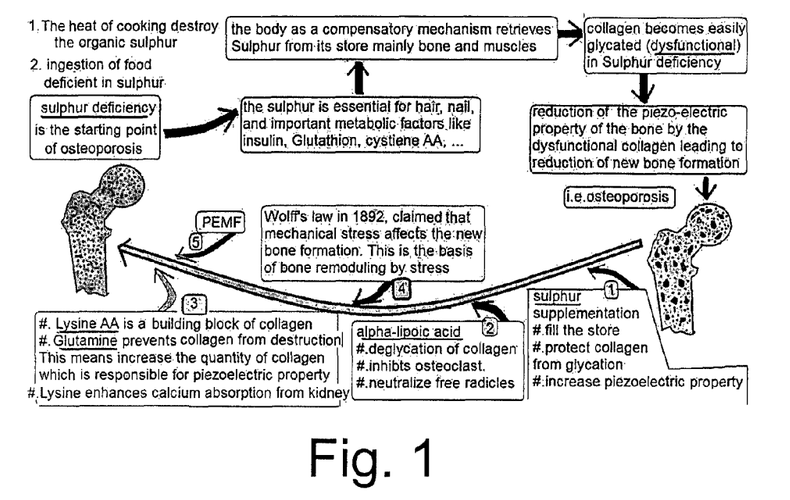
FIG. 1 is a diagram of the components of the regimen of the present invention in relation to its effect on the reversal of OP pathology.

The supplements above target the reduction of collagen bundles in OP pathology and facilitate favorable conditions for new bone formation. FIG. 1 shows how each of the components of the present invention work to reverse OP. In particular, FIG. 1 illustrates how healthy bone on the left portion of FIG. 1 undergoes osteoporotic transformation through OP pathology to form weakened OP bone on the right. The top of FIG. 1 details the OP pathology, the steps of: sulphur deficiency leading to removal of sulphur from bone collagen bundles; to dysfunctional collagen; to reduced bone formation; and how sedentary lifestyle further contribute to reduce bone formation, all leading to OP bone on the right. The bottom of FIG. 1 shows the components of the regimen and how each address OP pathology and contribute to the reversal of OP bone on the right back into healthy bone on the left. Sulphur supplementation, antioxidants and amino acids, components (a), (b), and (c), work to reverse dysfunctional bone collagen bundles and increase the amount of normal collagen bundles, leading way for mechanical energy stimulation of bone formation (6).&(19)&(20)

Figure 2:
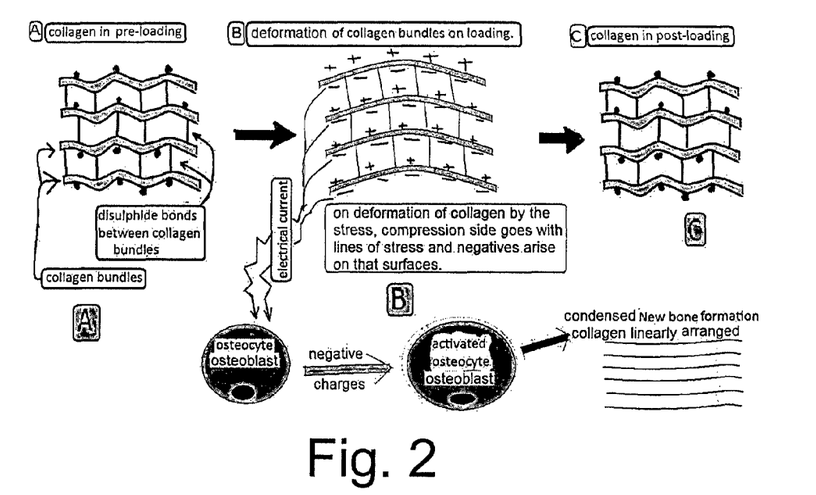
FIGS. 2a, 2b and 2c are diagrams showing the action of collagen bundles converting mechanical energy to electrical currents to stimulate bone formation.

Sulphur, antioxidants and amino acids supplementation correct the underlying pathology of OP, such that more functional collagen bundles work to convert mechanical energy to electrical current and thereby stimulate new bone formation as depicted in FIGS. 2a-2c. In particular, FIG. 2a illustrates collagen bundles and the disulphide bonds between the collagen bundles on pre-loading of stress. FIG. 2b illustrates the deformation of collagen bundles under stress and how this deformation leads to an electrical current that stimulates osteoblast new bone formation. FIG. 2c illustrates the return of the collagen bundles to the pre-loading conformation post-loading.

As shown in FIGS. 2a-2c, collagen bundles convert mechanical stress on bone into an electric current that then stimulates bone formation. More importantly, mechanical energy, such as in the form of exercise, stimulates bone formation by the process above at the lines of stress, leading to bone formation where it is most needed.

Figure 4:
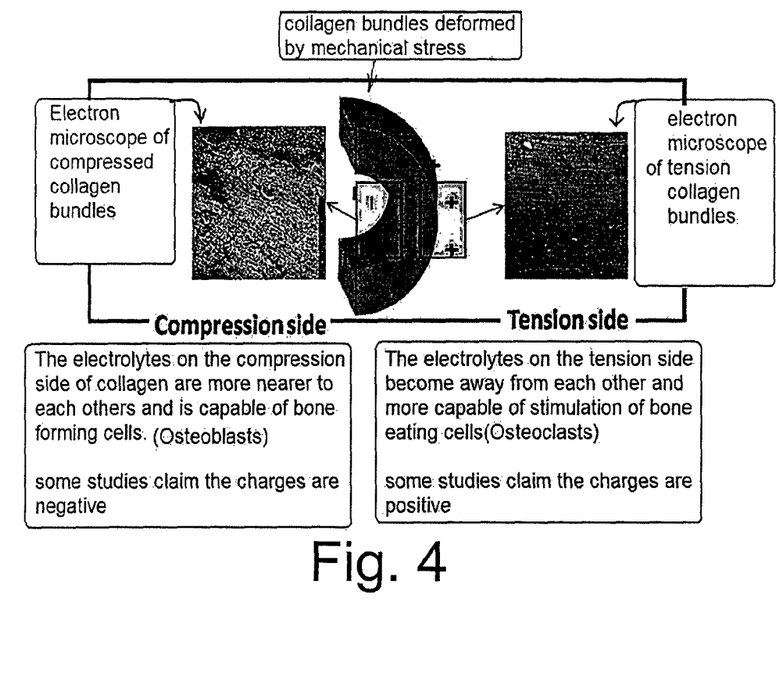
FIG. 4 is a diagram also showing the deformation of bone collagen bundle and the associated electrical charges. It further shows images of the sides of the collagen bundles under electron microscope and how the different charges on different sides of the collagen bundle stimulate bone reformation.

FIG. 4 further illustrates the specifics of the process of collagen bundle deformation illustrated in FIG. 2b. In particular, FIG. 4 illustrates how bone collagen deforms under stress, forming an electrical potential. Due to the deformation, the electrolytes on the compression side become closer to each other while the electrolytes on the tension side become further apart and are said to form negative and positive charges, respectively (7, 8). As seen in the illustration in the middle, the bone collagen bends and deforms with a compressed and a stretch side. FIG. 4 also shows the two sides: compressed and tension, under electron microscope. FIG. 4 shows how this conformation (or deformation under mechanical stress) creates negative charges on the compression side and positive charges on the tension side (7, 8). The negative charges of the compression side are capable of stimulation of bone forming cells (Osteoblasts and osteocytes) while the positive charges on the tension side are capable of stimulation of bone eating cells (Osteoclasts) (9).

The regimen of the present invention utilizes this natural process to stimulate bone formation. FIGS. 3a-3c depict the resulting bone formation of the present invention compared to current therapies. FIG. 3a illustrates the weight bearing point on the bone and the orientations of the lines of stress throughout the bone. FIG. 3b illustrates bone formation along the lines of stress with the treatment of the present invention regimen. Darker areas show denser bone formation along the lines of stress. Lighter regions show less dense bone formation away from the lines of stress. (i.e., biphasic normal new bone in accordance with the lines of the stress as explained earlier) FIG. 3c illustrates bone formation in treatment with current medications, specifically, bisphosphonates. As shown, compared to FIG. 3b of the present invention, new bone formation in FIG. 3c is evenly distributed throughout with no relation to the lines of stress when treated with bisphosphonates (i.e., an uniphasic bone of the same density).

Elderly individuals require more exercise than younger individuals in order to maintain bone integrity because of the reduction of bone formation. To enhance simulation of bone formation, a preferred embodiment of the present invention supplies mechanical energy in the form of exercise. It is also preferred that the exercise be on a regular daily basis.

However, regular exercise is sometimes difficult due to conditions such as: muscle weakness, painful arthritic joints, associated heart problems, or excess fat deposits are common in the elderly. In these situations, the addition of pulsed electromagnetic field (PEMF) to the regimen can decrease the need for vigorous exercise.

It is well known that PEMF can stimulate bone formation and thus has promising use in treatment of OP. PEMF supplementation acts as an external source of energy to bone tissues. Thus, the addition of PEMF to the regimen above lowers the need for vigorous exercise. PEMF compensates for the amount of energy needed and allows for new bone formation with moderate to mild exercise. In a preferred embodiment of this invention the optimal dose of PEMF is about ½ hours three times a week at an intensity of 0.6 Tesla and 30 Hz for a period of about 6 months.

PEMF may be administered by a PEMF device. The term "PEMF device" refers to any device capable of producing PEMF and application of PEMF to a subject. Examples of PEMF devices are shown in U.S. Pat. No. 5,478,303 (Foley-Nolan et al.); U.S. Pat. No. 5,518,496 (McLeod et al.); U.S. Pat. No. 6,132,362 (Tepper et al.); U.S. Pat. No. 6,179,772 (Blackwell); U.S. Pat. No. 6,261,221 (Tepper et al.); U.S. Pat. No. 6,418,345 (Tepper et al.); U.S. Pat. No. 6,524,233 (Markoll); U.S. Pat. No. 6,547,713 (Talpo); U.S. Pat. No. 6,839,595 (Tepper et al.); U.S. Pat. No. 7,175,587 (Gordon et al.); U.S. Pat. No. 8,376,925 (Dennis et al.); and in EP0048451A1 and EP1442766B1. All references cited herein are incorporated by reference.

The components of the regimen of this invention may be administered separately or at the same time or carefully coordinated times for optimal results. The regimen may be administered for a prolonged period, that is, for as long as the potential for osteoporotic bone or condition remains or the symptoms continue. In a preferred embodiment, the regimen is administered for a period of up to about 6 months. In another preferred embodiment, the regimen is administered for a period of up to about 2 years.

In accordance with another aspect of this invention, a kit of the components for effecting the regimen of this invention is provided for use by a patient with osteoporosis. For example, in one preferred embodiment of the kit, the oral dosages forms of the components are packaged in single dose packs comprising quantities sufficient of each supplement for a single dose. In a further embodiment, the kit comprises single dose packs in quantities sufficient for a period of about 6 months.

The term "oral dosage form" refers to any composition that can be taken by a subject through the mouth. For example, oral dosage forms maybe a solid or liquid: tablet, capsule, elixir, or suspension. The oral dosage forms can contain one of or up to a combination of all three of organic sulphur, antioxidants, or amino acids.

In formulating the dosage forms, the components, in the amounts described above, may be compounded according to accepted pharmaceutical practice with a physiologically acceptable vehicle, carrier, excipient, binder, preservative, stabilizer, flavor etc., in the particular type of unit dosage form.

The kit may include a number of unit dosages. Such kits can include a means for containing the dosages oriented in the order of their intended use. An example of a means for containing the dosages in the order of their intended use is a card. An example of such a kit is a "blister pack." Blister packs are well known in the packaging industry and are widely used for packaging pharmaceutical unit dosage forms. If desired, the blister can be in the form of childproof blister, i.e. a blister that is difficult for a child to open, yet can be readily opened by an adult. If desired, a memory aid can be provided, for example in the form of numbers, letters, or other markings or with a calendar feature and/or calendar insert, designating the days and the sections of a day in the treatment schedule in which the dosages can be administered, such as an AM dose is packaged with a "mid-day" and a PM dose; or an AM dose is packaged with a PM dose. Alternatively, placebo dosages, or vitamin or dietary supplements, either in a form similar to or distinct from the components, can be included.

The invention provides compositions, including preparations, formulations and/or kits, comprising combinations of ingredients, as described above (including the multi-ingredient combinations of components of the invention), that are serviceable as therapies for treating, preventing or improving conditions, states and disease symptoms involving OP. In one aspect, each member of the combination of components is manufactured in a separate package, kit or container; or, all or a subset of the combination of ingredients are manufactured in a separate package or container.

Table 1 set forth immediately below is a summary of the regimen of the present invention compared to current medication therapies of OP.

TABLE 1

| Subject Invention Regimen | Prior Art Regimen |
| --- | --- |
| 1. Organic sulphur supplementaion | 1. Bisphosponates (the principal drug) |
| 2. Certain A.A supplementation | 2. Vitamin D |
| 3. Certain Antioxidant | 3. Calcitnin hormone |
| 4. regular excercise | 4. Calcium supplementation |
| 5. PEMF | 5. Exercise (if possible) |
| New bone formation will be concentrated according to the lines of the stress. (i.e., biphasic bone similar to healthy normal one) | The new bone results from inhibtion of the resorption part of the bone turnover. Therefore, the new bone would be evenly distributed regardless of the stress line. (i.e., uniphasic bone) |
| The area away from the stress lines will have less new bone formation. | The bone is homogenously distributed throughout the bone surface area. |
| The bone along the lines of the stress is both more dense + some resilience (because collagen bundles are concentrated along these lines in linearly arrarranged pattern) + heavier + less vascular. | |
| The bone away from the lines of the stress in the rest of bone mass is less dense and more rigid (no resilience because collagen bundles are haphazardly oriented) + lighter + more vascular. | |
| The denser new bone along the stress lines. 1. The main support of the body weight. 2. Its resilience acts as shock absorbing mechanism to protect the bone. 3. denser + less vascular + heavier. | The bone is homogenously distributed. 1. It is less vacular than normal bone meaning avascular necrosis (AVN) may happen especially the jaw. 2. heavier than normal bone (more stress on muscles and joints presented by musculoskeletal pain). |
| The less denser bone away from the stress lines. 1. more rigid for muscles attachment 2. more vascular for blood supply to the bone. (reduce the incidence of AVN) 3. less bone concentration makes the bone lighter (decrease stress on muscles and joints) | 3. Although it is stronger than osteoporotic bone, it is still weaker than healthy normal bone. (porlonged utilization causes subtrochanteric fracture femur) |

TABLE 1-continued

| Subject Invention Regimen | Prior Art Regimen |
| --- | --- |
| 4. less dense Natural substances meaning no side effects. | Chemical compounds with side effects (12)<br>1. gastro-intestinal upset<br>2. headache, drowsiness, and fatiguability.<br>3. liver and renal toxicity<br>4. Musculoskeletal pain (caused by heavier bone)<br>5. Oesphgeal carcinoma (prolonged use)<br>6. subtrochanteric fracture femur<br>7. Osteonecrosis of the Jaw |
| Cheaper | Very expensive |
| 6 months is usually suffient for treatment of most cases | The treatment peroid may reach up to 2 years or more with a variable improvement. |

EXAMPLE

The following example describes an exemplary treatment regimen of the invention, using exemplary therapeutic combination compositions of the invention.

Example 1

Following the treatment regimen below for a period of 6 months:

| Components | Strength | Administration |
| --- | --- | --- |
| Organic sulphur | 1.5 grams | Twice a day |
| Alpha lipoic acid | 500-750 mg | Twice a day |
| Lysine | 500-1000 mg | Twice a day |
| Glutamine | 500-1000 mg | Twice a day |
| Exercise | Non vigorous | Three times a week |
| PEMF | ½ hour at 0.6 Tesla and 30 Hz | Three times a week |

REFERENCES

1. Wolff's law for bone adaptation in accordance with mechanical stress www.teambone.com/wolff.html
2. The explanation of bone adaptation under mechanical stress alexandria.tue.nl/repository/freearticles/585490.pdf
3. Sulphur is connectors between collagen bundles in the form of disulphide bonds. www.ncbi.nlm.nih.gov/books/NBK21582/4.
4. Sulphur prevents glycation because glucose will reduce sulphur instead of protein (collagen). Therefore, sulphur saves collagen from glycation. healthjournalclub.com/sulfur-obesity-and-glucose-metabolism/5.
5. Alpha-lipoic stops bone loss by inhibiting Osteoclast (bone eat cells) www.jimmunol.org/content/176/1/111.long
6. Mechanical stress on the bone is associated with new bone formation. www.rdpc.uevora.pt/bitstream/10174/5733/1/Polymeric%20piezoelectric%20actuator%20substrate%20for%20osteoblast%20mechanical%20stimulation.pdf
7. Mechanical stress on bone causes micro-deformation with generation electrical gradient difference on both sides of deformation. www.dowser.ca/piezoelectric.pdf
8. Electron microscopic studies showing electrical changes of collagen bundles associated with their deformation under the mechanical stress www.ciasem.com/PSD/Cusco2007/images-1/P370_ferreira.pdf
9. The deformation of collagen bundles shows that negative charges on compression side are capable of stimulation of bone forming cells. On the other side, the positive charges on tension side are capable of stimulation of Osteoclasts (bone eating cells). www.orthobullets.com/basic-science/9008/bone-remodeling
10. The trabeculae of proximal femur as an example of arrangement of lines of stress www3.ntu.edu.sg/bmerc/contents/JBPE/J001/JBPE%201(1);%2045-51.pdf
11. Biphosphonates mechanism of action and complications en.wikipedia.org/wiki/Bisphosphonate
12. Biphosphonates complications that may endanger the patient life. www.ncbi.nlm.nih.gov/pmc/articles/PMC2704135
13. the piezoelectric property of the bone is responsible for its continuous remoduling www.diva-portal.org/smash/get/diva2:20640/FULLTEXT01.pdf
14. The piezoelectric property of the bone is caused by the movements of lateral polar domain of the collagen (the movements of the electrolytes on the surface of the collagen bundles) www.iflysib.unlp.edu.ar/drupal/sites/default/files/Paper_2495_Mayosky 25_November_2010_proofread_by_RI.pdf
15. Alpha-lipoic has a strong anti-glycation property meaning converting dysfunctional collagen to functional one again www.anti-aging.gr.jp/english/pdf/2013/10(3) 4254.pdf
16. The discovery of the piezo-electric property of the bone is related to its collagen bundles. euro.ecom.cmu.edu/people/faculty/mshamos/Piezo1963.pdf
17. Lysine supplementation reduces calcium loss in the urine with subsequent strengthening of the bone. www.ncbi.nlm.nih.gov/pubmed/1486246
18. Lysine is an essential amino-acid that helps in treatment of osteoporosis www.thorne.com/altmedrev/.fulltext/12/2/169.pdf
19. The piezoelectric property of the bone arises from collagen-matrix interface as a result of deformation of collagen deformation under the effect of the mechanical stress.2009 www.ncbi.nlm.nih.gov/pmc/articles/PMC2771333/20.
20. The relative movement between the collagen bundles and the electrolytes of the bone matrix surrounding the bundles is responsible for the piezoelectric property of the bone. www.andrewamarino.com/PDFs/011-CalcTissRes1971.pdf

What is claimed is:
1. A therapeutic regimen for the treatment of osteoporosis comprising:
(a) organic sulphur administered at a dose of about 1.5 grams of organic sulphur twice a day,
(b) antioxidants administered at a dosage of 500-750 mg twice a day,

(c) amino acids administered at a dosage of 500-1000 mg twice a day,
(d) mechanical energy, wherein the mechanical energy comprises exercise, and
(e) pulsed electromagnetic field (PEMF), wherein the regimen stimulates bone formation, wherein the bone formed is biphasic bone.

2. The therapeutic regimen of claim 1, wherein the organic sulphur, the antioxidants and the amino acids are orally administered.

3. The therapeutic regimen of claim 2, wherein the amino acids comprise at least one of lysine or glutamine.

4. The therapeutic regimen of claim 3, wherein the amino acids comprise about 500-1000 mg of lysine administered twice a day.

5. The therapeutic regimen of claim 3, wherein the amino acids comprise about 500-1000 mg of glutamine administered twice a day.

6. The therapeutic regimen of claim 1, wherein the exercise is regular exercise.

7. The therapeutic regimen of claim 1, wherein the exercise is non-vigorous with the use of PEMF.

8. The therapeutic regimen of claim 7, wherein the PEMF is from a PEMF device.

9. The therapeutic regimen of claim 8, wherein the PEMF comprises application of PEMF for about ½ hour, three times a week at an intensity of about 0.6 Tesla and 30 Hz.

10. The therapeutic regimen of claim 1, wherein the regimen is administered for a period of up to about 6 months.

11. The therapeutic regimen of claim 1, wherein the regimen is administered for a period of up to about 2 years.

12. A kit comprising a PEMF device and the components of oral dosage forms of:
(a) organic sulphur wherein the oral dosage form of organic sulphur comprises about 1.5 grams of organic sulphur,
(b) antioxidants wherein the oral dosage form of antioxidants comprises 500-750 mg,
(c) amino acids wherein the oral dosage form of amino acids comprises 500-1000 mg, wherein the components are designed for use in combination with mechanical energy in a regimen for treatment of osteoporosis by stimulating new bone formation with instructions therefor.

13. The kit of claim 12, wherein the oral dosage form of the antioxidants comprise about 500-750 mg of alpha lipoic acid.

14. The kit of claim 12, wherein the oral dosage form of the amino acids comprise at least one of lysine or glutamine.

15. The kit of claim 12, wherein the oral dosage form of the amino acids comprise about 500-1000 mg of lysine.

16. The kit of claim 12, wherein the oral dosage form of the amino acids comprise about 500-1000 mg of glutamine.

17. The kit of claim 12, wherein the kit comprising each oral dosage form component in quantities sufficient for a regimen lasting about 6 months.

18. The kit of claim 12, wherein the kit contains single dose packs comprising the oral dosage forms of: (a) organic sulphur, (b) antioxidants, (c) amino acids; and directions for use.

* * * * *